(12) United States Patent
Narasimhan et al.

(10) Patent No.: US 7,166,137 B2
(45) Date of Patent: Jan. 23, 2007

(54) METHODS, COMPOSITIONS, AND KITS FOR COLORING HAIR

(75) Inventors: Saroja Narasimhan, Matawan, NJ (US); Lou Ann Christine Vena, Scotch Plains, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 324 days.

(21) Appl. No.: 10/983,368

(22) Filed: Nov. 8, 2004

(65) Prior Publication Data

US 2005/0097684 A1 May 12, 2005

Related U.S. Application Data

(60) Provisional application No. 60/519,175, filed on Nov. 12, 2003.

(51) Int. Cl.
*A61K 7/13* (2006.01)

(52) U.S. Cl. .................. 8/405; 8/410; 8/411; 8/412; 8/424; 132/202; 132/208; 424/70.1

(58) Field of Classification Search .............. 8/405, 8/410, 411, 412, 424; 132/202, 208; 424/70.1
See application file for complete search history.

(56) References Cited

U.S. PATENT DOCUMENTS

| | | | |
|---|---|---|---|
| 3,577,528 A | 5/1971 | McDonough | 424/70 |
| 3,629,330 A | 12/1971 | Brody | 260/553 |
| 4,511,360 A * | 4/1985 | Monnais et al. | 8/405 |
| 5,224,964 A | 7/1993 | Shami | 8/405 |
| 5,306,489 A | 4/1994 | Goldberg | 424/71 |
| 5,474,578 A | 12/1995 | Chan | 8/431 |
| 5,843,193 A | 12/1998 | Hawkins | 8/408 |
| 5,972,322 A | 10/1999 | Rath | 424/70.11 |
| 5,989,533 A | 11/1999 | Deegan | 424/70.28 |
| 6,007,585 A | 12/1999 | Syed | 8/432 |
| 6,045,591 A | 4/2000 | Deneulenaere | 8/426 |
| 6,206,935 B1 | 3/2001 | Onitsuka | 8/431 |
| 6,238,653 B1 | 5/2001 | Narasimhan | 424/62 |
| 6,306,182 B1 | 10/2001 | Chan | 8/426 |
| 6,315,989 B1 | 11/2001 | Narasimhan et al. | 424/62 |
| 6,440,177 B1 | 8/2002 | Orr | 8/426 |
| 6,596,035 B2 | 7/2003 | Gutkowski | 8/405 |
| 6,599,330 B2 | 7/2003 | Tian | 8/405 |
| 6,613,311 B2 | 9/2003 | Imperial | 424/62 |
| 6,669,933 B2 | 12/2003 | Duffer | 424/70.1 |
| 6,703,004 B2 | 3/2004 | Narasimhan et al. | 424/62 |
| 6,764,523 B2 | 7/2004 | Casperson | 8/405 |
| 6,770,103 B2 | 8/2004 | Patel | 8/405 |
| 2003/0074746 A1 | 4/2003 | Fischer | 8/405 |
| 2003/0154562 A1 | 8/2003 | Sarojini | 8/405 |
| 2004/0011370 A1 | 1/2004 | Vena | 132/116 |
| 2004/0016064 A1 | 1/2004 | Vena | 8/406 |
| 2004/0045101 A1 | 3/2004 | Miczewski | 8/406 |
| 2004/0047672 A1 | 3/2004 | Miczewski | 401/196 |
| 2004/0047674 A1 | 3/2004 | Geardino | 401/205 |
| 2004/0098814 A1 | 5/2004 | Au | 8/405 |
| 2004/0098816 A1 | 5/2004 | Au | 8/405 |
| 2004/0154108 A1 | 8/2004 | Narasimhan | 8/405 |

FOREIGN PATENT DOCUMENTS

GB 2 132 642 7/1984

OTHER PUBLICATIONS

Journal of Society of Cosmetic Chemists, vol. 35, pp. 297-310 (Sep./Oct. 1984).
Journal of Society of Cosmetic Chemists, vol. 36, pp. 1-16 (Jan./Feb. 1985).
Related U.S. Appl. No. 10/360,699, filed Feb. 6, 2003, Method and Compositions for Providing Natural Appearing Hair Color.
Related U.S. Appl. No. 10/454,405, filed Jun. 4, 2003, Methods, Compositions, and Kit for Coloring Hair.
Related U.S. Appl. No. 60/528,746, filed Dec. 11, 2003, Methods and Compositions for Coloring Hair.

* cited by examiner

*Primary Examiner*—Eisa Elhilo
(74) *Attorney, Agent, or Firm*—Julie Blackburn

(57) ABSTRACT

A method for oxidatively coloring hair comprising applying to the hair fibers a first composition comprising at least one oxidative dye operable to color hair when reacted with an oxidizing agent, said first composition being free of such oxidizing agent and thereby inoperative, by itself, to color hair; removing said first composition from the hair but leaving residual oxidative dye in contact with the hair fibers; applying, for a time, and in an amount sufficient to color the hair, a second composition to the hair fibers comprising at least one oxidizing agent reactive with the at least one oxidative dye in contact with the hair fibers after removal of the first composition; and a kit for use in practicing the method.

19 Claims, No Drawings

METHODS, COMPOSITIONS, AND KITS FOR COLORING HAIR

RELATED APPLICATIONS

This application claims priority from provisional patent application Ser. No. 60/519,175, filed Nov. 12, 2003.

TECHNICAL FIELD

The invention is in the field of methods for coloring hair, the compositions used in the method, and kits containing the various components necessary to practice the method.

BACKGROUND OF THE INVENTION

Commercially available hair color generally falls into one of three categories: permanent, semi-permanent, or temporary. The term "permanent" generally refers to oxidative hair color, which provides hair color that lasts about four to six weeks. While oxidatively colored hair remains permanently dyed, because of new hair growth, the roots must be re-colored about every four to six weeks. Oxidative hair color is usually sold in the form of a two-component kit. The preferred kits have one container filled with an aqueous alkaline composition in the liquid, gel, or creme form that contains oxidative dyes, and an alkalizing agent, which is most often ammonium hydroxide. In the other container is a developer composition that contains an oxidizing agent, usually hydrogen peroxide. The two components are mixed immediately prior to use and applied to hair. This mixture is left on the hair for an appropriate period of time, generally 30 to 60 minutes, then rinsed off with water.

It is estimated that about 50% of the female population colors their hair at home using such retail kits. Typically the process takes from 30 to 60 minutes, although Revlon sells one at-home retail kit under the High Dimension brand that is capable of oxidatively coloring hair in 10 minutes. Even though great strides have been made in reducing the time and complexity involved in oxidatively coloring hair, there are still consumers who believe that the process takes too long, or is simply too complex and inconvenient. Accordingly, hair color companies are on an eternal quest to make dyeing hair as simple and convenient as normal, every day grooming practices such as washing and conditioning hair. If coloring hair could be simplified so that it took only minutes and could be integrated into every day grooming practices, it is likely that many more consumers would use oxidative hair color, and those that do use it would use it more frequently. It is particularly desirable that the simple process be capable of permanently coloring hair.

It is an object of the invention to provide a method for oxidatively coloring hair in a process that can be integrated into normal every day grooming practices. The hair to be colored can be gray hair, hair already colored with oxidative, semi-permanent, or temporary dyes, or virgin hair of any color.

It is an object of the invention to provide a process for oxidatively coloring hair by applying first and second compositions sequentially.

It is an object of the invention to provide shampoo and conditioner compositions for oxidatively coloring hair as well as cleansing and conditioning hair.

It is an object of the invention to provide a kit for oxidatively coloring hair containing at least one shampoo and at least one conditioner composition.

It is a further object of the invention to provide a method for treating hair that has been oxidatively colored to rejuvenate and restore the hair color.

It is a further object of the invention to provide a method for providing dimensionality to oxidatively colored hair.

It is a further object to provide a method for oxidatively coloring hair wherein an oxidative dye composition is applied to the hair in an amount and for a time sufficient to cause at least some of the oxidative dye present to become entrapped within the hair fiber, removing the oxidative dyes that are not entrapped within the hair fiber, then treating the hair fibers with an oxidizing agent reactive with the trapped oxidative dye in the hair fibers to form color.

It is a further object of the invention to provide a color corrector for blondes to tone down the brassiness that may occur after a coloring or bleaching procedure.

SUMMARY OF THE INVENTION

The invention comprises a method for oxidatively coloring hair comprising:

(a) applying to the hair fibers a first composition comprising at least one oxidative dye operable to color hair when reacted with an oxidizing agent, said first composition being free of such oxidizing agent and thereby inoperative, by itself, to color hair;

(b) removing said first composition from the hair but leaving residual oxidative dye in contact with the hair fibers;

(c) applying, for a time, and in an amount sufficient to color the hair, a second composition to the hair fibers comprising at least one oxidizing agent reactive with the at least one oxidative dye in contact with the hair fibers after removal of the first composition.

The invention further comprises a method for maintaining and restoring the color vibrancy of oxidatively colored hair, or blending away gray hair comprising:

(a) applying to hair fibers a first composition comprising at least one oxidative dye operable to color hair when reacted with an oxidizing agent, said first composition being free of such oxidizing agent and thereby inoperative, by itself, to color hair;

(b) removing said first composition from the hair but leaving residual oxidative dye in contact with the hair fibers;

(c) applying, for a time, and in an amount sufficient to color the hair, a second composition to the hair fibers comprising at least one oxidizing agent reactive with the at least one oxidative dye in contact with the hair fibers after removal of the first composition.

The invention further comprises a kit containing a shampoo and conditioner composition, said kit comprised of:

(a) a first container containing a shampoo composition comprising at least one oxidative dye operable to color hair when reacted with an oxidizing agent, said shampoo composition being free of such oxidizing agent and thereby inoperative, by itself, to color hair;

(b) a second container containing a conditioner composition comprising at least one oxidizing agent reactive with the at least one oxidative dye present in the shampoo composition.

The invention further comprises a kit containing a conditioner and a shampoo composition, said kit comprised of:

(a) a first container containing a conditioner composition comprising at least one oxidative dye operable to color hair when reacted with an oxidizing agent, said conditioner composition being free of such oxidizing agent and thereby inoperative, by itself, to color hair;

(b) a second container containing a shampoo composition comprising at least one oxidizing agent reactive with the at least one oxidative dye present in the conditioner composition.

DETAILED DESCRIPTION

The invention comprises a method for oxidatively coloring hair, blending away gray hair, or treating hair that has been chemically processed to restore or rejuvenate color, or improve dimensionality, comprising:

(a) applying to hair fibers a first composition comprising at least one oxidative dye operable to color hair when reacted with an oxidizing agent, said first composition being free of such oxidizing agent and thereby inoperative, by itself, to color hair;

(b) removing said first composition from the hair but leaving residual oxidative dye in contact with the hair fibers;

(c) applying, for a time, and in an amount sufficient to color the hair, a second composition to the hair fibers comprising at least one oxidizing agent reactive with the at least one oxidative dye in contact with the hair fibers after removal of the first composition.

The invention further comprises a method for reducing brassiness of blonde hair that has been oxidatively dyed, bleached or highlighted, or reducing the appearance of highlights in hair that has been highlighted comprising the steps of:

(a) applying to the hair fibers a first composition comprising at least one oxidative dye operable to color hair when reacted with an oxidizing agent, said first composition being free of such oxidizing agent and thereby inoperative, by itself, to color hair;

(b) removing said first composition from the hair but leaving residual oxidative dye in contact with the hair fibers;

(c) applying, for a time, and in an amount sufficient to color the hair, a second composition to the hair fibers comprising at least one oxidizing agent reactive with the at least one oxidative dye in contact with the hair fibers after removal of the first composition.

First, the compositions used in the method of the invention will be explained in detail.

I. The Compositions Used in the Method.

A. The First Composition

The first composition that is applied to hair may be in a variety of forms, including shampoo, solution, suspension, conditioner, hair gel, or the like. Particularly preferred is where the first composition is a shampoo or conditioner. The first composition contains oxidative dyes that, when exposed to an oxidizing agent, are operable to form color on the hair. However, the first composition does not contain any oxidizing agent that is capable of reacting with the oxidative dyes that are present to form color. Hence, the oxidative dyes present in the first composition are inactive. Generally, while the first composition contains at least one oxidative dye, but not oxidizing agent, the first composition will often appear straw colored, or similarly light colored, and if a portion of such composition is daubed onto the hand it will not color the skin. This is in stark contrast to what would be seen if an oxidizing agent were added to the first composition and reacted with the oxidative dyes present. In that case, if a portion of such mixture were daubed onto the skin, the mixture would dye the skin a color similar to the dye color that would be applied to the hair.

The first composition is an aqueous based composition generally comprising at least one oxidative dye. The first composition generally will comprise from about 0.01–95%, preferably about 0.05–95%, preferably about 0.1–85% by weight of the total composition of water. The composition may be in the form of a solution or emulsion. If the latter, the emulsion generally comprises from about 0.01–95%, preferably about 0.05–85%, more preferably about 0.1–80% by weight of the total composition of water and about 0.01–80%, preferably about 0.1–65%, preferably about 0.5–50% by weight of the total composition of an oily phase. The first composition may comprise a variety of other ingredients as further described herein.

1. Oxidative Dyes (a). Primary Intermediates.

The first composition comprises at least one primary intermediate and, optionally, at least one coupler for the formation of oxidative dyes. Suitable ranges of primary intermediates are about 0.0001–6%, preferably about 0.0005–5.5%, more preferably about 0.001–5% by weight of the total composition. Such primary intermediates are well known for use in hair color, and include ortho or para substituted aminophenols or phenylenediamines, including para-phenylenediamines of the formula:

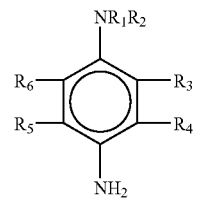

wherein $R_1$ and $R_2$ are each independently hydrogen, $C_{1-6}$ alkyl, or $C_{1-6}$ alkyl substituted with one or more hydroxy, methoxy, methylsulphonylamino, aminocarbonyl, furfuryl, unsubstituted phenyl, or amino substituted phenyl groups; $R_3$, $R_4$, $R_5$, and $R_6$ are each independently hydrogen, $C_{1-6}$ alkyl, $C_{1-6}$ alkoxy, halogen, or $C_{1-6}$ alkyl substituted with one or more hydroxy or amino groups.

Specific examples of suitable primary intermediates include para-phenylenediamine, 2-methyl-1,4-diaminobenzene, 2,6-dimethyl-1,4-diaminobenzene, 2,5-dimethyl-1,4-diaminobenzene, 2,3-dimethyl-1,4-diaminobenzene, 2-chloro-1,4-diaminobenzene, 2-methoxy-1,4-diaminobenzene, 1-phenylamino-4-aminobenzene, 1-dimethylamino-4-aminobenzene, 1-diethylamino-4-aminobenzene, 1-bis(beta-hydroxyethyl)amino-4-aminobenzene, 1-methoxyethylamino-4-aminobenzene, 2-hydroxymethyl-1,4-diaminobenzene, 2-hydroxyethyl-1,4-diaminobenzene, 2-isopropyl-1,4-diaminobenzene, 1-hydroxypropylamino-4-aminobenzene, 2,6-dimethyl-3-methoxy-1,4-diaminobenzene, 1-amino-4-hydroxybenzene, and derivatives thereof, and acid or basic salts thereof.

Preferred primary intermediates are p-phenylenediamine, p-aminophenol, o-aminophenol, N,N-bis(2-hydroxyethyl)-p-phenylenediamine, 2,5-diaminotoluene, their salts and mixtures thereof.

(b). Color Coupler

The first composition may optionally comprise from about 0.0001–10%, more preferably about 0.0005–8%, most preferably about 0.001–7% by weight of the total oxidative composition of one or more color couplers. Suitable color couplers include, for example, those having the general formula:

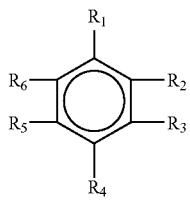

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, catechol, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methyl pyrazolone, 3,4-methylenedioxyphenol, 3,4-methylenedioxy-1-[(beta-hydroxyethyl)amino]benzene, 1-methoxy-2-amino-4-[(beta-hydroxyethyl)amino]benzene, 1-hydroxy-3-(dimethylamino)benzene, 6-methyl-1-hydroxy-3[(beta-hydroxyethyl)amino]benzene, 2,4-dichloro-1-hydroxy-3-aminobenzene, 1-hydroxy-3-(diethylamino)benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl)amino-3-aminobenzene, 2-methyl-1,3-diaminobenzene, 6-methoxy-1-amino-3-[(beta-hydroxyethyl)amino]-benzene, 6-(beta-aminoethoxy)-1,3-diaminobenzene, 6-(beta-hydroxyethoxy)-1-amino-3-(methylamino)benzene, 6-carboxymethoxy-1,3-diaminobenzene, 6-ethoxy-1-bis(beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diamionphenoxyethanol, and mixtures thereof.

Preferred couplers include resorcinol, 1-naphthol, 2-methylresorcinol, 4-amino-2-hydroxy toluene, m-aminophenol, 2,4-diaminophenoxyethanol, phenyl methyl pyrazolone, their salts, or mixtures.

In the hair color industry, hair color is classified into one of ten levels as follows:
1=very black
2=bright black
3=very dark brown
4=dark brown
5=medium brown
6=light brown
7=dark blonde
8=medium blonde
9=light blonde
10=high lift blonde Set forth in the table below is a non-limiting example of the primary intermediates and optional color couplers that may be used in the first composition, and which are known to provide various shades of hair color. Other primary intermediates and couplers may be used in addition to, or in lieu of, those set forth in the Table and nothing herein shall be construed to limit the invention to only those primary intermediates and couplers set forth.

| Level 1 - Very Black | | Level 2 - Bright Black | |
| --- | --- | --- | --- |
| Primary Intermediates | Couplers | Primary Intermediates | Couplers |
| p-phenylenediamine | m-aminophenol | p-phenylenediamine | resorcinol |
| p-phenylenediamine sulfate | resorcinol | 2-chloro-P-phenylenediamine sulfate | |
| 2-chloro-phenylenediamine sulfate | 4-amino-2-hydroxytoluene | o-aminophenol | |
| p-aminophenol | 4-chlororesorcinol | | |
| o-aminophenol | m-aminophenol HCL | | |
| | 2,4-diaminophenoxy ethanol | | |
| | m-phenylenediamine sulfate | | |

| Level 3 - Very Dark Brown | | Level 4 - Dark Brown | |
| --- | --- | --- | --- |
| Primary Intermediates | Couplers | Primary Intermediates | Couplers |
| p-phenylenediamine | resorcinol | p-phenylenediamine | resorcinol |
| N,N-bis(2-hydroxyethyl)-P-phenylenediamine sulfate | 1-naphthol | N,N-bis(2-hydroxyethyl)-P-phenylene diamine sulfate | 1-naphthol |
|  | m-aminophenol | p-aminophenol | m-aminophenol phenyl methyl pyrazolone |
|  |  | o-aminophenol | 4-amino-2-hydroxytoluene |

| Level 5 - Medium Brown | | Level 6 - Light Brown | |
| --- | --- | --- | --- |
| Primary Intermediates | Couplers | Primary Intermediates | Couplers |
| p-phenylenediamine | resorcinol | p-phenylenediamine | resorcinol |
| N,N-bis(2-hydroxyethyl)-P-phenylenediamine sulfate | 1-naphthol | N,N-bis(2-hydroxyethyl)-P-phenylenediamine sulfate | 1-naphthol |
| p-aminophenol | m-aminophenol | p-aminophenol | m-aminophenol |
| o-aminophenol | phenyl methyl pyrazolone |  | phenyl methyl pyrazolone |
|  | 2-methylresorcinol |  | 4-amino-2-hydroxytoluene |
|  | 4-amino-2-hydroxtoluene |  | 2-methylresorcinol |

| Level 7 - Dark Blonde | | Level 8 - Medium Blonde | |
| --- | --- | --- | --- |
| Primary Intermediates | Couplers | Primary Intermediates | Couplers |
| p-phenylenediamine | resorcinol | p-phenylenediamine | resorcinol |
| N,N-bis(2-hydroxyethyl)-P-phenylenediamine sulfate | 1-naphthol | N,N-bis(2-hydroxyethyl)-P-phenylenediamine sulfate | 1-naphthol |
| p-aminophenol | phenyl methyl pyrazolone | p-aminophenol | m-aminophenol |
| o-aminophenol |  |  | phenyl methyl pyrazolone |
|  |  |  | 4-amino-2-hydroxytoluene |

| Level 9 - Light Blonde | | Level 10 - High Lift Blonde | |
| --- | --- | --- | --- |
| Primary Intermediates | Couplers | Primary Intermediates | Couplers |
| p-phenylenediamine | resorcinol | p-phenylenediamine | resorcinol |
| N,N-bis(2-hydroxyethyl)-P-phenylenediamine sulfate | 4-amino-2-hydroxytoluene | N,N-bis(2-hydroxyethyl)-P-phenylenediamine sulfate | 1-naphthol |
| p-aminophenol | phenyl methyl pyrazolone |  | phenyl methyl pyrazolone |
| o-aminophenol | 2-methylresorcinol |  | 2-methylresorcinol |
|  | 1-naphthol |  |  |

2. Alkalizing Agents

The first composition preferably comprises one or more alkalizing agents. The term "alkalizing agent" means an ingredient that is capable of imparting alkalinity (e.g. a pH of greater than 7) to the first composition. Preferably, the pH of the first composition ranges from about 7.0 to 12.0, more preferably from about 7.5 to 11.5.

A variety of alkalizing agents are suitable, and, if present, generally range from about 0.0001–15%, preferably about 0.005–10%, more preferably about 0.01–5% based on the total weight of the first composition. Suitable alkalizing agents include ammonium hydroxide, metal hydroxides, alkanolamines, sodium silicate, metal sulfites, metal carbonates, sodium metasilicate, and mixtures thereof. Suitable metal hydroxides and carbonates include alkali metal and alkaline earth metal hydroxides, sulfites, or carbonates. Examples of such metal hydroxides include sodium, potassium, lithium, calcium, magnesium and so on; and of metal sulfites are sodium, potassium, or calcium sulfite. A particularly preferred metal sulfite is sodium sulfite. Suitable alkanolamines include mono-, di-, and trialkanolamines such as monoethanolamine (MEA), diethanolamine (DEA), triethanolamine (TEA), 2-aminobutanol, aminoethyl propanediol, aminomethyl propanediol, bis-hydroxyethyl tromethamine, diethanolamine, diethyl ethanolamine, diisopropanolamine, dimethylamino methylpropanol, dimethyl MEA, isopropanolamine, methylethanolamine, mixed isopropanolamines, triisopropanolamine, tromethamine, and mixtures thereof. A particularly preferred alkanolamine is MEA.

The alkalizing agent present in the first composition may react with other ingredients in the mixture in situ, such as fatty acids, proteins or hydrolyzed proteins, if present. Depending on the amount of alkalizing agent present and the presence or absence of ingredients that will react with the alkalizing agent, it is possible that the alkalizing agent may be completely reacted in situ, partially reacted in situ, or not reacted at all if there are no other ingredients in the composition that will react with the alkalizing agent.

Most preferred is where the first composition comprises at least one alkalizing agent, preferably in an amount sufficient to provide a composition having a pH of greater than about 7.0 to about 12.0.

In the most preferred embodiment of the invention the first composition contains sodium sulfite in addition to a second alkalizing agent selected from sodium hydroxide, alkanolamine, or metal hydroxide. Preferably the second alkalizing agent is an alkanolamine, specifically monoethanolamine.

3. Thickening Agents

The first composition may contain one or more thickening agents. If present, suitable ranges are from about 0.001–25%, preferably 0.005–20%, more preferably about 0.01–15% by weight of the total composition. Preferably the first composition contains one or more thickening agents that increase the viscosity of the composition such that when it is applied to hair it doesn't run.

A variety of thickening agents are suitable including low melting point waxes, synthetic polymeric thickeners, cellulosic thickeners, and the like.

Examples of low melting point waxes include emulsifying wax, and fatty alcohols having the formula R—OH wherein R is a straight or branched chain, unsaturated or unsaturated alkyl having from about 4 to 35, more preferably about 6 to 22, carbon atoms. Examples of such fatty alcohols include stearyl alcohol, cetearyl alcohol, behenyl alcohol, and the like.

Examples of synthetic polymeric thickeners include polymers of acrylic acid, methacrylic acid and their simple esters, which may be co-polymerized with one or more organic groups such as ethoxylated or propoxylated polymeric moieties. Examples of such synthetic polymeric thickeners include acrylamides copolymer, acrylates/behenth-25 methacrylate copolymer, acrylates C10–30 alkyl acrylate crosspolymer, acrylates ceteth-20 itaconate copolymer, acrylates/steareth-50 acrylate copolymer, acrylates/stearyl methacrylate copolymer, acrylates/vinyl isodecanoate crosspolymer, or mixtures theref.

Examples of cellulosic based thickeners include cellulose gum as well as alkyl and hydroxylalkyl derivatives of celluloses and methyl or ethyl cellulose, such as hydroxyethylcellulose, hydroxypropylcellulose, hydroxyethyl ethylcellulose, hydroxybutyl celluose, or mixtures thereof.

In the most preferred embodiment of the invention, the compositions contain at least one thickener, which is cellulose or a cellulose derivative.

4. Surfactants

The first composition preferably comprises one or more surfactants that may assist in maintaining the composition in the emulsion form if it is an emulsion, or aid in the foaming or cleansing capability of the composition if it is in the shampoo form. Suitable surfactants include anionic surfactants, nonionic surfactants, amphoteric surfactants, and the like. If present, surfactants may range from about 0.001–50%, preferably about 0.005–45%, more preferably about 0.1–40% by weight of the first composition.

(a) Nonionic Surfactants

Suggested ranges of nonionic surfactant, if present, are about 0.01–10%, preferably about 0.05–8%, more preferably about 0.1–7% by weight of the total oxidative composition. Suitable nonionic surfactants include alkoxylated alcohols or ethers, alkoxylated carboxylic acids, sorbitan derivatives, and the like.

Suitable alkoxylated alcohols, or ethers, are formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include steareth 2–30, which is formed by the reaction of stearyl alcohol and ethylene oxide where the number of repeating ethylene oxide units is 2 to 30; Oleth 2–30 which is formed by the reaction of oleyl alcohol and ethylene oxide where the number of repeating ethylene oxide units is 2 to 30; Ceteareth 2–100, formed by the reaction of a mixture of cetyl and stearyl alcohol with ethylene oxide, where the number of repeating ethylene oxide units in the molecule is 2 to 100; Ceteth 1–45 which is formed by the reaction of cetyl alcohol and ethylene oxide, and the number of repeating ethylene oxide units is 1 to 45, and so on.

Also suitable as the nonionic surfactant are alkyoxylated carboxylic acids, which are formed by the reaction of a carboxylic acid with an alkylene oxide or with a polymeric ether. The resulting products have the general formula:

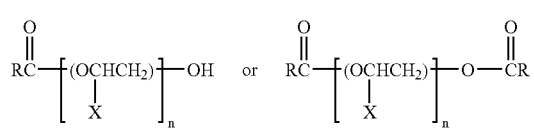

where RCO is the carboxylic ester radical, X is hydrogen or lower alkyl, and n is the number of polymerized alkoxy groups. In the case of the diesters, the two RCO— groups do not need to be identical. Preferably, R is a $C_{6-30}$ straight or branched chain, saturated or unsaturated alkyl, and n is from 1–100.

Also suitable are various types of alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate, sorbitan stearate, and so on.

(b) Anionic Surfactants

If desired the first composition may contain one or more anionic surfactants. Preferred ranges of anionic surfactant are about 0.01–25%, preferably 0.5–20%, more preferably 1–15% by weight of the total oxidative composition. Suitable anionic surfactants include alkyl and alkyl ether sulfates generally having the formula $ROSO_3M$ and $RO(C_2H_4O)_x SO_3M$ wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula:

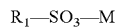

$$R_1{-\!-}SO_3{-\!-}M$$

wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

Also suitable as anionic surfactants are reaction products of fatty acids esterified with isethionic acid and neutralized with sodium hydroxide, or fatty acids reacts with alkanolamines or ammonium hydroxides. The fatty acids may be derived from coconut oil, for example. Examples of fatty acids also include lauric acid, stearic acid, oleic acid, palmitic acid, and so on.

In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sultones, which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts.

Still another class of anionic surfactants include N-acyl amino acid surfactants and salts thereof (alkali, alkaline earth, and ammonium salts) having the formula:

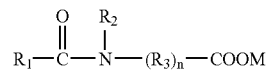

wherein $R_1$ is a $C_{8-24}$ alkyl or alkenyl radical, preferably $C_{10-18}$; $R_2$ is H, $C_{1-4}$ alkyl, phenyl, or $-CH_2COOM$; $R_3$ is $CX_2$- or $C_{1-2}$ alkoxy, wherein each X independently is H or a $C_{1-6}$ alkyl or alkylester , n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

(c). Cationic, Zwitterionic or Betaine Surfactants

Certain types of amphoteric, zwitterionic, or cationic surfactants may also be used as the amphiphilic surface active material. Descriptions of such surfactants are set forth in U.S. Pat. No. 5,843,193, which is hereby incorporated by reference in its entirety.

Amphoteric surfactants that can be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

Suitable amphoteric surfactants may be imidazolinium compounds having the general formula:

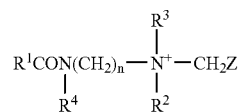

wherein $R^1$ is $C_{8-22}$ alkyl or alkenyl, preferably $C_{12-16}$; $R^2$ is hydrogen or $CH_2CO_2M$, $R^3$ is $CH_2CH_2OH$ or $CH_2CH_2OCH_2CHCOOM$; $R^4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation such as an alkali metal, alkaline earth metal, ammonium, or alkanol ammonium cation. Examples of such materials are marketed under the tradename MIRANOL, by Miranol, Inc.

Also suitable amphoteric surfactants are monocarboxylates or dicarboxylates such as cocamphocarboxypropionate, cocoamphocarboxypropionic acid, cocamphocarboxyglycinate, and cocoamphoacetate.

Other types of amphoteric surfactants include aminoalkanoates of the formula

$$R{-\!-}NH(CH_2)_n COOM$$

or iminodialkanoates of the formula:

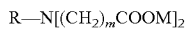

$$R{-\!-}N[(CH_2)_m COOM]_2$$

and mixtures thereof; wherein n and m are 1 to 4, R is $C_{8-22}$ alkyl or alkenyl, and M is hydrogen, alkali metal, alkaline earth metal, ammonium or alkanolammonium. Examples of such amphoteric surfactants include n-alkylaminopropionates and n-alkyliminodipropionates, which are sold under the trade name MIRATAINE by Miranol, Inc. or DERIPHAT by Henkel, for example N-lauryl-beta-amino propionic acid, N-lauryl-beta-imino-dipropionic acid, or mixtures thereof.

Zwitterionic surfactants are also suitable for use in the compositions of the invention. The general formula for such surfactants is:

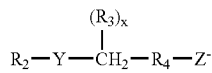

wherein $R_2$ contains an alkyl, alkenyl or hydroxy alkyl radical of from about 8 to about 18 carbon atoms, from 0 to about 10 ethylene oxide moieties and 0 or 1 glyceryl moiety; Y is selected from the group consisting of nitrogen, phosphorus, and sulfur atoms; $R_3$ is an alkyl or monohydroxyalkyl group containing about 1 to 3 carbon atoms; X is 1 when Y is a sulfur atom, and 2 when Y is a nitrogen or phosphorus atom; $R_4$ is an alkylene or hydroxyalkylene of from about 1 to about 4 carbon atoms, and Z is a radical selected from the group consisting of carboxylate, sulfonate, sulfate, phosphonate, and phosphate groups.

Zwitterionic surfactants include betaines, for example higher alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxylethyl betaine, and mixtures thereof Also suitable are sulfo- and amido-betaines such as coco dimethyl sulfopropyl betaine, stearyl dimethyl sulfopropyl betaine, and the like.

(d). Polar Solvents

The first composition may also comprise a variety of polar solvents other than water, including mono-, di-, or polyhydric alcohols, and similar water soluble ingredients. If present, such polar solvents may range from about 0.01–25%, preferably about 0.05–15%, more preferably about 0.1–10% by weight of the first composition of polar solvent. Examples of suitable monohydric alcohols include ethanol, isopropanol, benzyl alcohol, butanol, pentanol, ethoxyethanol, and the like. Examples of dihydric, or polyhydric alcohols, as well as sugars and other types of humectants that may be used include glucose, fructose, mannose, mannitol, malitol, lactitol, inositol, and the like. Suitable glycols include propylene glycol, butylene glycol, ethylene glycol, polyethylene glycols having from 4 to 250 repeating ethylene glycol units, ethoxydiglycol, and the like. Many of these types of alcohols also serve also serve as penetration enhancers, meaning that they enhance penetration of primary intermediates and couplers into the hair shaft by virtue of their tendency to act as humectants and swell the hair shaft. Ethoxydiglycol is a particularly good penetration enhancer and is the preferred polar solvent.

In the preferred embodiment of the invention the composition comprises water in addition to one or more polar solvents, which are dihydric alcohols. In the preferred compositions, about 0.001–20%, preferably about 0.005–10%, more preferably about 0.001–8% by weight of the total composition comprises a non-aqueous polar solvent.

(e) Chelating Agents

The first composition may also contain 0.0001–5%, preferably 0.0005–3%, more preferably 0.001–2% of one or more chelating agents which are capable of complexing with and inactivating metallic ions in order to prevent their adverse effects on the stability or effects of the composition. In particular, the chelating agent will chelate the metal ions found in the water and prevent these ions from interfering with the deposition and reaction of the dye with the hair fiber surface. Suitable chelating agents include EDTA and calcium, sodium, or potassium derivatives thereof, HEDTA, sodium citrate, TEA-EDTA, and so on.

(f). pH Adjusters

It may also be desireable to add small amounts of acids or bases to adjust the pH of the first composition to the desired pH range of greater than about 7.0 to 12.0. Suitable acids include hydrochloric acid, phosphoric acid, erythorbic acid, and the like. Suitable bases include sodium hydroxide, potassium hydroxide, and the like. Also suitable are primary, secondary, or tertiary amines or derivative thereof such as aminomethyl propanol, monoethanolamine, and the like. Suggested ranges of pH adjusters are from about 0.00001–8%, preferably about 0.00005–6%, more preferably about 0.0001–5% by weight of the total composition.

(g). Preservatives

The first composition may also contain one or more preservatives. Suggested ranges are about 0.0001–8%, preferably 0.0005–7%, more preferably about 0.001–5% by weight of the total composition. Suitable preservatives include methyl, ethyl, and propyl paraben, hydantoins, and the like.

In the preferred method of the invention the first composition is in the form of a shampoo that the user can apply to the hair much in the manner of a normal shampoo. The composition preferably comprises from about:

0.1–40% surfactant,
0.1–99.9% water,
0.0001–6% of at least one primary intermediate and, optionally about 0.0001–10% of at least one coupler.

Preferably the surfactant comprises one or more anionic, zwitterionic, or betaine surfactants which are capable of providing a cleansing and foaming effect that approximates shampoo. Most preferred is where the surfactant comprises one or more anionic surfactants.

B. The Second Composition

The second composition contains at least one oxidizing agent that is reactive with the at least one oxidative dye present in the first composition to form color on hair. The second composition may be in a wide variety of forms, including but not limited to solutions, shampoos, suspensions, hair conditioners, spray on liquids, and so on, provided that it contains as a minimum, the at least one oxidizing agent. The second composition is preferably in the aqueous form and comprises from about 0.01–99%, preferably about 0.05–95%, more preferably about 0.1–90% by weight of the total second composition of water. The other ingredients that may be found in the second composition include, but are not limited to, those set forth below.

1. Oxidizing Agent

The second composition comprises at least one oxidizing agent that is reactive with the primary intermediate and optional coupler in the first composition to form color on hair. The oxidizing agent may be present ranging from about 0.001–50%, preferably about 0.005–45%, more preferably about 0.01–40% by weight of the total composition. Preferably the oxidizing agent is hydrogen peroxide, although other suitable peroxides such as urea peroxide, sodium perborate, etc. may be used as well. Preferably, the hydrogen peroxide concentration in the second composition may range all the way from a 1 or 2 volume peroxide concentration up to 30 volume peroxide, the second composition preferably comprising about 5 volume peroxide. However, if desired, the second composition may comprise 10, 20, 25, or 30 volume peroxide, or any whole or fractional number in between the stated volume numbers.

2. Hair Conditioning Ingredients

When the second composition is in the form of a hair conditioner or similar composition, it may be desirable to include one or more ingredients that provide a conditioning effect to the hair. Preferably the second composition comprises one or more of such conditioners. A variety of conditioners are suitable including cationic quaternary ammonium compounds, cationic polymers, oily conditioning agents, fatty alcohols, proteins, and so on. If present, such conditioners may range from about 0.01–45%, preferably 0.5–20%, more preferably 1–15% by weight of the total composition.

(a). Cationic Quaternary Ammonium Compounds

Suitable cationic conditioning agents include cationic quaternary ammonium salts. Examples of such salts include those having the formula:

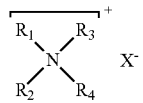

wherein $R_1$ is an aliphatic group of 1 to 22 carbon atoms, or aromatic, aryl, or alkaryl group having 12 to 22 carbon atoms; $R_2$ and $R_3$ are each independently an aliphatic group having 1–22 carbon atoms; and $R_4$ is an alkyl group of from 1 to 3 carbon atoms, and X is an anion selected from halogen, acetate, phosphate, nitrate and methyl sulfate radicals. The aliphatic groups may contain, in addition to carbon atoms, ether linkages as well as amido groups. Suitable quaternary ammonium compounds may be mono-long chain alkyl, di-long chain alkyl, tri-long chain alkyl, and the like. Examples of such quaternary ammonium salts include behenalkonium chloride, behentrimonium chloride, behentrimonium methosulfate, benzalkonium chloride, benzethonium chloride, benzyl triethyl ammonium chloride, cetalkonium chloride, cetrimonium chloride, cetrimonium bromide, cetrimonium methosulfate, cetrimonium tosylate, cetylpyridinium chloride, dibehenyl/diarachidyl dimonium chloride, dibehenyldimonium chloride, dibehenyldimonium methosulfate, dicapryl/dicaprylyl dimonium chloride, Other quaternary ammonium salts that may be used as a conditioning agent include compounds of the general formula:

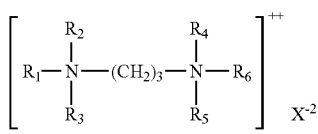

wherein $R_1$ is an aliphatic group having 16 to 22 carbon atoms, $R_2$, $R_3$, $R_4$, $R_5$, and $R_6$ are the same or different and are selected from alkyls having 1 to 4 carbon atoms and X is an anion as above defined.

Also, quaternary imidazolinium salts having the following general formula are suitable as conditioning agents:

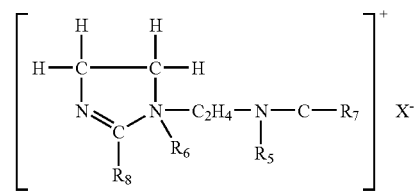

wherein $R_5$ is hydrogen or a $C_{1-4}$ alkyl; $R_6$ is a $C_{1-4}$ alkyl; $R_7$ is a $C_{8-22}$ alkyl; and $R_8$ is hydrogen, or a $C_{1-22}$ alkyl; and X is an anion as defined above.

(b). Amide or Amine Conditioning Agents

Amides which exhibit the general formulas set forth below are also suitable conditioning agents:

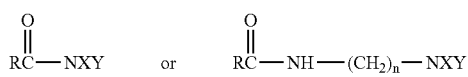

wherein R is a straight or branched chain saturated or unsaturated alkyl having 6 to 30 carbon atoms, n is an integer from 1 to 4, and X and Y are each independently H, or $C_{1-6}$ lower alkyl.

Preferred is an Amide of the Formula:

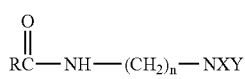

wherein R is a $C_{12-22}$ straight or branched chain alkyl, n is an integer from 1 to 4, and X is lower alkyl, preferably methyl.

Also suitable are amidoamine salts, which are the condensation products of fatty acids th a polyfunctional amines, for example, those having the formula RCONH $(CH_2)_n NR_1 R_2$ where RCO is a fatty acyl group such as stearoyl, $R_1$ and $R_2$ are methyl or ethyl, and n is 2 or 3. Examples of such compounds include stearmidopropyl dimethylamine. Particularly preferred are amidoamine compounds complexed with a mild dimer acid, such as di(behenamidopropyl dimethyl amine) dimer dilinoleate or di(linoleamidopropyl dimethyl amine) dimer linoleate. Both ingredients are sold by Alzo, Inc. under the NECON tradename.

Also suitable are salts of fatty primary, secondary, or tertiary amines, wherein the substituted groups have 12 to 22 carbon atoms. Examples of such amines include dimethyl stearamine, dimethyl soyamine, stearylamine, myristylamine, tridecylamine, ethyl stearamine, and so on.

(d). Cationic Polymers

Also suitable as conditioning agents are a variety of cationic polymers including but not limited to those set forth below:

1. Quaternized Cellulose Ethers

Suitable conditioning agents include quaternary derivatives of cellulose ethers such as polymers sold under the tradename JR-125, JR-400, JR-30M.

2. Copolymers of Vinyl Pyrrolidone

Copolymers of vinylpyrrolidone are suitable conditioning agents, including but not limited to those having monomer units of the formula:

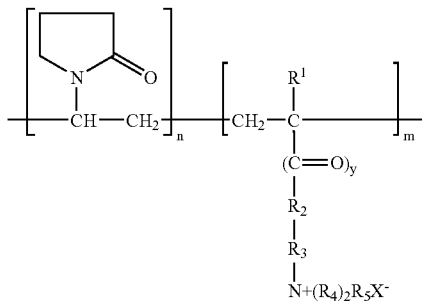

wherein $R^1$ is hydrogen or methyl, preferably methyl;
y is 0 or 1, preferably 1
$R^2$ is O or NH, preferably NH;
$R^3$ is $C_xH_{2x}$ where x is 2 to 18, or —$CH_2$—CHOH—$CH_2$—, preferably $C_xH_{2x}$ where x is 2;
$R^4$ is methyl, ethyl, phenyl, or $C_{1-4}$ substituted phenyl, preferably methyl; and
$R^5$ is methyl or ethyl, preferably methyl.

3. Acrylic Polymers

Suitable conditioning agents also include homopolymers of dimethyldiallylammonium chloride, or copolymers of dimethyldiallylammonium chloride and acrylamide. Such compounds are sold under the tradename MERQUAT by Merck. Also suitable are various types of homo- or copolymers derived from acrylic or methacrylic acid, selected from monomer units acrylamide, methylacrylamide, diacetoneacrylamide, acrylamide or methacrylamide substituted on the nitrogen by lower alkyl, alkyl esters of acrylic acid and methacrylic acid, vinylpyrrolidone, or vinyl esters.

4. Cationic Silicones

Cationic silicones are also suitable conditioning agents. As used herein, the term "cationic silicone" means any silicone polymer or oligomer having a silicon backbone, including polysiloxanes, having a positive charge on the silicone structure itself. Cationic silicones that may be used in the compositions of the invention include those corresponding to the following formula:

$(R)_aG_{3-a}$—Si—(—$OSiG_2$)$_n$—(—$OSiG_b(R_1)_{2-b}$)$_m$—
O—$SiG_{3-a}(R_1)_a$ in which G is selected from the group consisting of H, phenyl, OH, $C_{1-10}$ alkyl, and is preferably $CH_3$; and a is 0 or an integer from 1 to 3, and is preferably 0; b is 0 or 1, preferably 1; the sum n+m is a number from 1 to 2,000 and is preferably 50 to 150; n is a number from 0 to 2000, and is preferably 50 to 150; and m is an integer from 1 to 2000, and is preferably 1 to 10; and $R_1$ is a monovalent radical of the formula $C_qH_{2q}L$ in which q is an integer from 2 to 8 and L is selected from the groups:

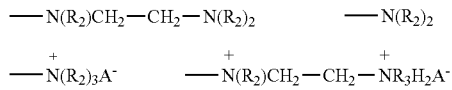

in which $R_2$ is selected from the group consisting of H, phenyl, benzyl, a saturated hydrocarbon radical, and is preferably an alkyl radical containing 1–20 carbon atoms; and A- is a halide ion.

Also suitable are diquaternary polydimethylsiloxanes such as Quatemium-80, sold by Goldschmidt Corporation under the tradename ABIL-Quat 3272.

Examples of other cationic polymers that can be used in the compositions of the invention are disclosed in U.S. Pat. Nos. 5,240,450 and 5,573,709, which are hereby incorporated by reference.

(e) Oily Conditioning Agents

Also suitable as conditioning agents are a variety of oily materials that provide good conditioning effect to hair. Suitable oils are liquid at room temperature and may comprise esters, hydrocarbons, and the like. Examples of such oily conditioning agents include, but are not limited to those set forth below:

1. Silicones

Also suitable as oily conditioning agents are one or more silicones. Suitable silicone hair conditioning agents include volatile or nonvolatile nonionic silicone fluids, silicone resins, and silicone semi-solids or solids.

Volatile silicones are linear or cyclic silicones having a measureable vapor pressure, which is defined as a vapor pressure of at least 2 mm. of mercury at 20° C. Examples of volatile silicones are cyclic silicones having the general formula:

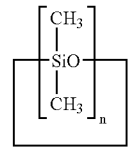

where n=3–7.

Also, linear volatile silicones that may be used in the compositions of the invention have the general formula:

$(CH_3)_3Si$—O—[$Si(CH_3)_2$—O]$_n$—$Si(CH_3)_3$ where n=0–7, preferably 0–5.

Also suitable are water insoluble nonvolatile silicone fluids including polyalkyl siloxanes, polyaryl siloxanes, polyalkylaryl siloxanes, polyether siloxane copolymers, amine-functional silicones, and mixtures thereof. Such silicones have the following general formula:

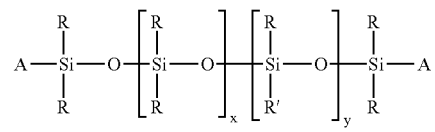

wherein R and R' are each independently alkyl, aryl, or an alkyl substituted with one or more amino groups, and x and y are each independently 0–100,000, with the proviso that x+y equals at least one and A is siloxy endcap unit. Preferred is where A is methyl, R is methyl, and R' is an alkyl substituted with at least two amino groups, most preferably an amine-functional silicone having the formula:

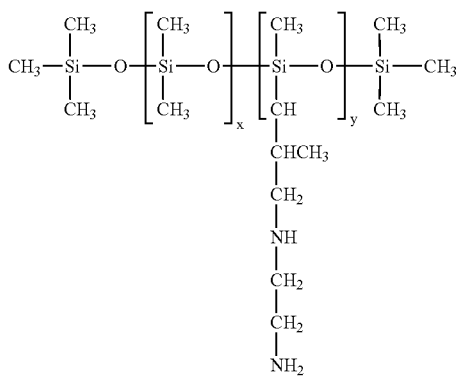

which is known by the CTFA name trimethylsilylamodimethicone.

Another type of silicone hair conditioning agent may also be a silicone polymer having the following general formula:

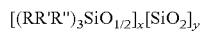

wherein R, R' and R" are each independently a $C_{1-10}$ straight or branched chain alkyl or phenyl, and x and y are such that the ratio of $(RR'R'')_3SiO_{1/2}$ units to $SiO_2$ units is 0.5 to 1 to 1.5 to 1.

Preferably R, R' and R" are a $C_{1-6}$ alkyl, and more preferably are methyl and x and y are such that the ratio of $(CH_3)_3SiO_{1/2}$ units to $SiO_2$ units is 0.75 to 1. Most preferred is this trimethylsiloxy silicate containing 2.4 to 2.9 weight percent hydroxyl groups which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Coming Corporation under the tradename 2-0749 and 2-0747, each of which is a blend of about 40–60% volatile silicone and 40–60% trimethylsiloxy silicate. Dow Coming 2-0749, in particular, is a fluid containing about 50% trimethylsiloxy silicate and about 50% cyclomethicone. The fluid has a viscosity of 200–700 centipoise at 25° C., a specific gravity of 1.00 to 1.10 at 25° C., and a refractive index of 1.40–1.41.

2. Organic Oils

Also suitable are various types of organic oils including esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like, as well as the esters disclosed on pages 1670–1676 of the *C.T.F.A. International Cosmetic Ingredient Dictionary and Handbook, Eighth Edition,* 2000, which is hereby incorporated by reference in its entirety.

The organic oil may also comprise glyceryl esters of fatty acids, or triglycerides, such as castor oil, lanolin oil, triiso- cetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as the oil are glyceryl esters (excluding fats and oils which are glyceryl esters of fatty acids) which are primarily fatty acid mono-di- and triglycerides which are modified by reaction with other alcohols, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the organic oil are nonvolatile hydrocarbons such as isoparaffins, hydrogenated polyisobutene, mineral oil, squalene, petrolatum, and so on.

Also suitable as the oil are various lanolin derivatives such as acetylated lanolin, acetylated lanolin alcohol, and so on.

Also suitable as the oil are various fluorinated oils are fluoro guerbet esters or perfluropolyethers. Suitable perfluoropolyethers are disclosed in U.S. Pat. Nos. 5,183,589, 4,803,067, 5,183,588 all of which are hereby incorporated by reference. These perfluoropolyethers are commercially available from Montefluos under the trademark Fomblin.

Other suitable oils include sorbitan derivatives such as PEG sorbitan beeswax, PEG sorbitan isostearate, PEG sorbitan lanolate, PEG sorbitan laurate, PEG sorbitan oleate, PEG sorbitan palmitate, PEG sorbitan stearate, polysorbates, sorbitan trioleates, sorbitan sesquioleates, sorbitan stearates, sorbitan tristearates, and so on.

(f). Sunscreens

The second composition may also comprise sunscreens, which are various ingredients that will provide a screening effect when the hair is exposed to sunlight, and thereby reduce the tendency of the color of the hair to fade. A variety of sunscreens are suitable, including hydroxyphenylbenzotriazole compounds that are capable of absorbing ultraviolet radiation in the wavelength range of 200 to 400 nanometers, preferably about 250 to 390 nanometers.

Suitable 2-hydroxyphenyl benzotriazole compounds for use in the compositions of the invention correspond to one of the the general formulas (a), (b) and (c), set forth below:

Formula (a) compounds have the general formula:

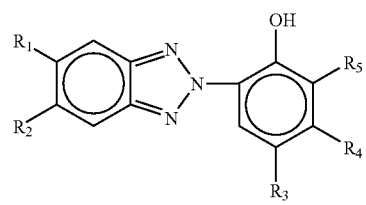

wherein $R_1$, $R_2$, $R_3$, $R_4$, and $R_5$ are each independently H, hydroxyl, carboxyl, halogen, or $C_{1-40}$ straight or branched chain alkyl, $C_{1-40}$ straight or branched chain alkoxy, $C_{2-20}$ alkoxycarbonyl, $C_{1-40}$ alkyl substituted phenyl, $C_{5-6}$ cycloalkyl, $SO_3H$, $SO_3Na$, or

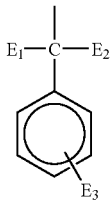

wherein $E_1$ and $E_2$ are each independently H or $C_{1-4}$ alkyl, and $E_3$ is H, halogen, or $C_{1-4}$ alkyl; $R_3$ is H, halogen, OH, $C_{1-40}$ straight or branched chain alkyl, $SO_3Na$, $C_{5-6}$ cycloalkyl, phenyl, $C_{1-10}$ alkyl substituted phenyl, or

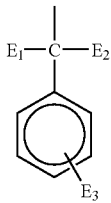

wherein $E_1$ and $E_2$ are each independently H, or $C_{1-4}$ alkyl, and $E_3$ is H, halogen, or $C_{1-4}$ straight or branched chain alkyl.

Examples of such compounds are disclosed in U.S. Pat. Nos. 5,240,975; 4,904,712; 4,921,966; 5,097,041; 5,095,062; 4,973,701; 4,587,346; and 4,675,352.

Preferred are compounds wherein $R_1$ and $R_2$ are both H. A more preferred subset are those compounds wherein $R_1$ and $R_2$ are both H, and $R_3$ is $SO_3Na$ or $SO_3H$. A preferred subset of the latter group are those compounds wherein $R_1$, $R_2$ and $R_4$ are H, $R_3$ is $SO_3Na$ or $SO_3H$, and $R_5$ is a $C_{1-10}$ straight or branched chain alkyl. Most preferred is a compound wherein $R_1$, $R_2$, and $R_4$ are H, $R_3$ is $SO_3Na$, and $R_5$ is a $C_{1-10}$ branched chain alkyl. Once example is the compound having the CTFA name sodium benzotriazolyl butyl phenol sulfonate,. This material may be purchased from Ciba-Geigy under the tradename Cibafast W Liquid, which is an anionic material.

The second composition may also contain the same surfactants, preservatives, pH adjusters, solvents, and other ingredients as found in the first composition and in the same ranges.

Preferred is where the second composition is in the form of a hair conditioner comprising, by weight of the total composition:
  about 0.01–99% water,
  about 0.001–50% oxidizing agent, and
  about 0.01–45% of one or more hair conditioning agents.

Preferably the oxidizing agent comprises hydrogen peroxide, and the hair conditioning agent comprises at least one silicone.

Most preferred is wherein the second composition has a pH ranging from about 1.5 to 6.9, preferably about 3.0 to about 6.0.

II. The Method

Depending on the selection of the dyes and other ingredients in the first and second compositions, the method of the invention is capable of providing a variety of desirable effects. It is possible to rejuvenate the color of chemically processed hair so that the faded color looks vibrant and fresh. It is also possible to dye gray hair, or in the case where the consumer has only a small percentage of gray hair, blend that gray hair away. In addition, with proper selection of the first and second composition components, it is possible to provide dimensionality, tone, and unique visual effects to virgin or chemically processed hair that may make it look more natural. The term "chemically processed" means hair that has been dyed by permanent, semi-permanent, or temporary colors, or has been bleached, permed, or relaxed.

In the method of the invention the first composition as described herein is applied to the hair for a period of time sufficient to permit at least some of the oxidative dye present to permeate into the hair shaft. Because the pH of the first composition is in the alkaline range, it will cause the hair shaft to swell, or open, slightly, permitting the oxidative dyes present therein to enter the hair shafts. The first composition may be applied to wet or dry hair, however it is preferred that the first composition be applied to wet hair. Generally, the amount of time required for at least some of the oxidative dye present to permeate the hair shaft may from 0.5 to 20 minutes, but is preferably from about 1–5, more preferably about 1.5 to 2.5 minutes. In the most preferred embodiment of the invention the first composition is in the form of a shampoo having a pH of greater than 7.0 to about 12.0. The consumer applies the shampoo to her hair and cleanses the hair in the normal manner for the appropriate period of time, preferably about 2 minutes, then removes the composition from the hair. While the first composition may be removed from the hair in a variety of ways (for example, by toweling or sluicing out the excess), preferred is where the first composition is removed from the hair by rinsing with water. Even during the relatively short period of time where the first composition is exposed to the hair, at least some of the oxidative dye molecules present in the first composition will permeate into the hair shaft and become trapped in the hair shafts such that when the first composition is removed from the hair, preferably by rinsing with water, a portion of the oxidative dye that has permeated into the hair shaft remains therein and is not rinsed or removed from the hair in the removal step.

The second composition is then applied to the hair for an appropriate period of time to cause the oxidative dyes present to react with the oxidizing agent present in the second composition to form color on the hair. As noted, the preferred second composition is a hair conditioner containing a low volume of oxidizing agent (hydrogen peroxide). The conditioner composition is applied to the hair for an appropriate period of time, ranging from about 0.5 to 5 minutes, preferably about 1–3 minutes. The oxidative hair dye trapped within the hair shafts will oxidize upon contact with the oxidizing agent present in the second composition and the hair becomes colored. The resulting method provides cleaner color because extraneous dye is washed away and is not incidentally oxidized on skin, scalp or surrounding areas when the second composition containing the oxidizing agent is applied.

The method of the invention provides an excellent way to restore hair color, or rejuvenate hair that has been colored, and will also color gray hair or blend away gray hair. In addition, treating virgin or oxidatively colored hair with the first and second compositions may provide unique visual effects and dimensionality to treated hair.

The method of the invention provides a way to maintain hair color via normal grooming processes that are conducted on a daily basis. Particularly, when the first and second compositions are in the form of shampoo and conditioner respectively, the method of the invention can be incorporated into daily grooming rituals with very little, if any inconvenience.

III. The Kit

The invention further comprises a kit containing the components necessary to practice the method of the invention. The kit will contain at least two containers. The first container is filled with the first composition as described herein, which is preferably a shampoo. The second container is filled with the second composition, which is preferably a hair conditioner composition. The two containers, which are preferably in the form of bottles, may be shrink wrapped together similar to how soda cans are shrinkwrapped, such that the consumer can select the shampoo composition that most nearly complements her hair color and purchase the shampoo/conditioner combo together. Or the two containers may be bound together using various types of plastic binders or similar engagements. It is also possible for the shampoo conditioner containers to be sold as part of an oxidative hair dye kit. In that case, the kit would contain an oxidative dye composition, a developer composition, and containers containing the first and second compositions of the invention. The consumer would combine the oxidative dye and developer composition and color the hair with that mixture. At some time after the oxidative hair color procedure had been performed, particularly when the consumer might start noticing that her hair color was looking faded or washed out, she would use the shampoo and conditioner compositions found in the kit in washing and conditioning hair, and this would result in rejuvenation and, at least, partial restoration of the hair color. The shampoo and conditioner compositions would be used at desired intervals by the consumer to restore the color of her hair.

The method, compositions, and kit can be used for a variety of applications. For example, it is an excellent method for use by blondes who wish to tone down the brassy looking tones that sometimes occur after their original hair color has washed out. The method also provides a way to subdue previously highlighted hair where the consumer is no longer satisified with the highlights and wants to return to a less multi-tonal appearance.

The invention will be further described in connection with the following examples, which are set forth for the purposes of illustration only.

EXAMPLE 1

Standard oxidative hair color compositions were prepared as follows:

| Ingredient | 45 (burgundy brown) % | 50 (medium brown) % | 60 (light brown) % |
|---|---|---|---|
| Water | QS | QS | QS |
| Erythorbic acid | 0.20 | 0.20 | 0.20 |
| Sodium sulfite | 0.50 | 0.50 | 0.50 |
| Ethoxydiglycol | 5.00 | 5.00 | 5.00 |
| Tetrasodium EDTA | 0.80 | 0.80 | 0.80 |
| Ethanolamine | 3.00 | 3.00 | 3.00 |
| *Hypnea Musciformis* extract, *gellidiela acerosa* extract, *sargassum filpensdula* extract, sorbitol | 0.80 | 0.80 | 0.80 |
| Sodium benzotriazolyl butylphenol sulfonate, buteth-3, tributyl citrate | 0.50 | 0.50 | 0.50 |
| P-phenylenediamine | 1.25 | 0.63 | 0.40 |
| N,N-bis(2-hydroxyethyl)-P-phenylenediamine sulfate | — | 0.11 | 0.06 |
| P-aminophenol | 0.35 | — | — |
| Resorcinol | 0.75 | 0.50 | 0.33 |
| 4-amino-2-hydroxytoluene | 0.95 | — | — |
| Phenyl methyl pyrazolone | 0.05 | — | — |
| 1-naphthol | — | 0.04 | 0.08 |
| M-aminophenol | — | 0.07 | 0.04 |
| Ammonium lauryl sulfate | 2.00 | 2.00 | 2.00 |
| Oleic acid | 12.50 | 12.50 | 12.50 |
| Cetearyl alcohol | 4.00 | 4.00 | 4.00 |
| Emulsifying wax | 2.00 | 2.00 | 2.00 |
| Oleth-20 | 1.00 | 1.00 | 1.00 |
| Steareth-21 | 0.70 | 0.70 | 0.70 |
| *Limanthes Alba* (meadowfoam seed) oil | 0.75 | 0.75 | 0.75 |
| Oleyl alcohol | 0.40 | 0.40 | 0.40 |
| Polyquaternium-10 | 0.50 | 0.20 | 0.20 |
| Polyquaternium-28 | 0.50 | 0.50 | 0.50 |
| Mica, titanium dioxide | 0.30 | 0.30 | 0.30 |
| Hydrolyzed wheat protein | 0.50 | 0.50 | 0.50 |
| Fragrance | 1.25 | 1.25 | 1.25 |
| Ammonium hydroxide (28% in water) | 9.00 | 9.00 | 9.00 |

The oxidative dye compositions were prepared by combining the ingredients and mixing well.

EXAMPLE 2

Standard developer, or oxidizing agent, compositions were prepared as follows:

| Ingredient | % by weight |
|---|---|
| Water | QS |
| Methylparaben | 0.05 |
| EDTA | 0.02 |
| Mineral oil | 0.60 |
| Cetearyl alcohol/ceteareth-20 | 4.50 |
| Lauramide MEA | 0.01 |
| Cetearyl alcohol | 0.20 |
| Cyclomethicone/trimethylsiloxysilicate (50:50) | 0.01 |
| Trimethylsilylamodimethicone, C11–15 pareth-7, C12–16 pareth-9, trideceth-12, glycerin, water | 2.00 |
| Hydrogen peroxide (35% in water) | 22.50 |
| Steareth-10 allyl ether/acrylates copolymer | 0.20 |
| Disodium phosphate | 0.03 |
| Phosphoric acid | 0.03 |

The composition was prepared by combining the ingredients and mixing well to form an emulsion.

EXAMPLE 3

First compositions (shampoos) for use in the method of the invention were made as follows:

|  | Shampoo Shade | | | | | |
| --- | --- | --- | --- | --- | --- | --- |
| Ingredient | 35 velvet brown | 45 burgundy brown | 50 medium brown | 50S medium brown | 55 medium auburn | 74 copper blonde |
| Water | QS | QS | QS | QS | QS | QS |
| Erythorbic acid | 0.50 | 0.50 | 0.50 | 0.50 | 0.50 | 0.50 |
| Sodium sulfite | 0.50 | 0.50 | 0.50 | 0.50 | 0.50 | 0.50 |
| Ethoxydiglycol | 2.00 | 2.00 | 2.00 | 2.00 | 2.00 | 2.00 |
| P-phenylenediamine | 1.63 | 1.25 | 1.25 | 2.00 | 0.49 | — |
| P-aminophenol | 0.53 | 0.35 | 0.35 | — | 0.76 | 0.56 |
| Resorcinol | 0.77 | 0.75 | 0.75 | 1.00 | — | — |
| 4-amino-2-hydroxytoluene | 0.90 | 0.95 | 0.95 | — | 0.42 | 0.85 |
| M-aminophenol | 0.18 | — | — | — | 0.42 | — |
| P-phenylenediamine sulfate | 0.15 | — | — | — | — | — |
| Phenyl methyl pyrazolone | — | 0.05 | 0.05 | — | 0.03 | 0.09 |
| P-aminophenol | — | — | — | — | — | 0.56 |
| O-aminophenol | — | — | — | — | — | 0.25 |
| Hydroxypropylmethylcellulose | 0.30 | 0.30 | 0.30 | 0.30 | 0.30 | 0.30 |
| Tetrasodium EDTA | 0.30 | 0.30 | 0.30 | 0.30 | 0.30 | 0.30 |
| Sodium lauryl sulfate (30% in water) | 10.00 | 10.00 | 10.00 | 10.00 | 10.00 | 10.00 |
| Sodium laureth sulfate (28% in water) | 20.00 | 20.00 | 20.00 | 20.00 | 20.00 | 20.00 |
| Cocamidopropyl betaine (35%) | 4.00 | 4.00 | 4.00 | 4.00 | 4.00 | 4.00 |
| Ethanolamine | 2.50 | 2.50 | 2.50 | 2.50 | 2.50 | 2.50 |
| Isostearic acid | 6.00 | 6.00 | 6.00 | 6.00 | 2.50 | 2.50 |
| Lauramide DEA (82–86%) | 2.00 | 2.00 | 2.00 | 2.00 | 2.00 | 2.00 |
| Fragrance oil | 0.75 | 0.75 | 0.75 | 0.75 | 0.75 | 0.75 |

The above shampoo compositions were prepared by combining the ingredients and mixing well. The compositions were, in general, straw-colored liquid compositions having a viscosity similar to shampoo.

EXAMPLE 4

A second composition (hair conditioner) for use in the method of the invention having a 5 volume concentration of hydrogen peroxide was prepared as follows:

| Ingredient | % |
| --- | --- |
| Water | QS |
| Methyl paraben | 0.20 |
| Propyl paraben | 0.05 |
| Panthenol | 0.01 |
| Behentrimonium chloride | 4.00 |
| Glycerin | 5.00 |
| Cetearyl alcohol | 3.00 |
| Mango seed butter | 4.50 |
| Amodimethicone, trideceth-12, cetrimonium chloride | 1.50 |
| Sodium benzotriazolyl butyl phenol sulfonate, buteth-3, tributyl citrate | 0.01 |
| Fragance | 0.50 |
| Cholesteryl oleyl carbonate, cholesteryl chloride, cholesteryl nona?? | 0.01 |
| Isostearyl lactate, diiosostearyl malate, triisostearyl citrate, isostearyl glycolate | 0.01 |
| Citric acid | 0.02 |
| Methylchloroisothiazolinone | 0.04 |
| Hydrogen peroxide (35% in water) | 4.50 |

The composition was prepared by combining the ingredients and mixing well.

EXAMPLE 5

The shampoo and conditioner compositions used in the method of the invention were used to treat 1.5 gram 95% gray hair swatches that were oxidatively colored with High Dimension Burgundy Brown (45), and High Dimension Medium Brown (50) oxidative hair color as set forth in Example 1. About 1 part oxidative dye was combined with about 1.5 parts of the developer composition of Example 2. The mixtures were applied to the hair swatches for ten minutes and rinsed off with water. The swatches were then treated with the shampoo composition from Example 3 that matched the color of the color used to oxidatively color the hair. For example, the hair swatches oxidatively colored with High Dimension Burgundy Brown (45) dye were shampooed with the Burgundy Brown (45) shampoo composition of Example 3. Similarly the hair swatches oxidatively colored with High Dimension Medium Brown (50) were shampooed with the Medium Brown (50) shampoo composition of Example 3. The swatches were shampooed for two minutes, then rinsed well with water. The hair conditioner of Example 4 was applied to the swatches for 2 minutes then rinsed well with water. The chromaticity of the hair swatches was measured with a datacolor color tools QC (version 1.2.1) spectrocolorimeter from the values of $a^*$, $b^*$, in the $L^*$, $a^*$, and $b^*$ international color notation system. The degree of lightening was determined from the change in L (lightening), a (red), and b (yellow) values. The results were as follows:

| SWATCH | L | a | b | ΔL | ΔE |
| --- | --- | --- | --- | --- | --- |
| 95% gray hair, untreated | 65.23 | 1.49 | 18.92 | | |
| Dyed with Burgundy Brown (45) oxidative Color | 26.38 | 12.68 | 6.5 | | |
| Dyed with Burgundy Brown (45) oxidative color + Shampoo (45) + conditioner | 23.37 | 10.99 | 4.44 | −3.01 | 4.03 |
| Dyed with Medium Brown (50) oxidative color | 32.8 | 3.22 | 9.39 | | |

-continued

| SWATCH | L | a | b | ΔL | ΔE |
|---|---|---|---|---|---|
| Dyed with Medium Brown (50) oxidative color + shampoo (50) + conditioner | 30.12 | 3.27 | 8.44 | −2.68 | 2.84 |

The above results show that the shampoo/conditioner treatment gave the swatches a more multi-layered, or dimensional effect. Dimensionality makes oxidatively colored hair appear much more natural looking.

EXAMPLE 6

The shampoo and conditioner compositions used in the method of the invention were used to treat 1.5 gram 95% gray hair swatches that were oxidatively colored with High Dimension Light Brown (60) oxidative hair color as set forth in Example 1. About 1 part oxidative dye was combined with about 1.5 parts of the developer composition of Example 2. The mixture was applied to the hair swatches for ten minutes and rinsed off with water. Each respective set of swatches was treated with shampoo compositions 35, 45, 50S, and 74 from Example 3. For example, one set of hair swatches oxidatively colored with High Dimension Light Brown (60) dye were shampooed with the shampoo composition (35) of Example 3. Similarly the hair swatches oxidatively colored with High Dimension Light Brown (60) were shampooed with the shampoo composition 45 of Example 3, and so on. The swatches were shampooed for two minutes, then rinsed well with water. The hair conditioner of Example 4 was applied to the swatches for 2 minutes then rinsed well with water. The chromaticity of the hair swatches was measured with a datacolor color tools QC (version 1.2.1) spectrocolorimeter from the values of a*, b*, in the L*, a*, and b* international color notation system. The degree of lightening was determined from the change in L (lightening), a (red), and b (yellow) values. The results were as follows:

| SWATCH | L | a | b | ΔL | ΔE |
|---|---|---|---|---|---|
| High Dimension Light Brown Control | 37.9 | 4.06 | 7.67 | | |
| Shampoo Composition 35 + conditioner | 26.93 | 5.43 | 3.7 | −10.97 | 11.75 |
| Shampoo Composition 45 + conditioner | 30.67 | 8.75 | 7.32 | −7.24 | 8.63 |
| Shampoo Composition 50S + conditioner | 29.26 | 4.73 | 8.01 | −8.64 | 8.67 |
| Shampoo Composition 74 + conditioner | 33.36 | 6.49 | 8.71 | −4.54 | 5.26 |

The above results show that the various shampoo/conditioner treatments gave the swatches a more multi-layered, or dimensional effect. Dimensionality makes oxidatively colored hair appear much more natural looking.

EXAMPLE 7

The shampoo and conditioner compositions used in the method of the invention were used to treat 1.5 gram 95% gray hair swatches. Hair swatches were treated with shampoo compositions 35, 45, and 50 from Example 3. For example, one set of hair swatches treated with shampoo 35 by shampooing the swatch for 2 minutes then rinsing well with water. The hair conditioner of Example 4 was then applied to the swatch for 2 minutes, then rinsed well with water. Each set of hair swatches was similarly treated with the different shampoos and conditioner. The chromaticity of the hair swatches was measured with a datacolor color tools QC (version 1.2.1) spectrocolorimeter from the values of a*, b*, in the L*, a*, and b* international color notation system. The degree of lightening was determined from the change in L (lightening), a (red), and b (yellow) values. The results were as follows:

| SWATCH | L | a | b | ΔL | ΔE |
|---|---|---|---|---|---|
| 95% gray hair | 65.23 | 1.49 | 18.92 | — | — |
| Shampoo Composition 35 + conditioner | 35.98 | 6.68 | 5.8 | | |
| Shampoo Composition 45 + conditioner | 41.56 | 9.17 | 6.29 | | |
| Shampoo Composition 50 Medium Brown + conditioner | 52.65 | 2.13 | 8.96 | | |

It can be seen that, depending on the dyes used, varying tones are obtained on gray hair.

EXAMPLE 8

The following experiments were conducted to show the efficacy of the technology on bleached hair. Seven light brown virgin hair swatches weighing 1.5 grams each were bleached using Revlon Frost & Glow Bleach Blonding kit. The bleach was applied to the swatches for 1 hour, then rinsed off with water. The conditioner composition in the Frost & Glow kit was applied to the hair and rinsed out with water. The L, a, b values of the hair swatches vs. control (untreated swatch was measured using a DataColor Colorimeter where L is the is the level of darkness or lightness, a is the red and green components, and b is yellow and blue components.

| Hair Types | L | a | b |
|---|---|---|---|
| Light brown untreated virgin hair (control) | 32.80 | 6.47 | 13.07 |
| Light brown virgin hair treated with Frost & Glow bleach treatment | 63.53 | 8.01 | 30.68 |

After one week, six of the seven swatches bleached as noted above were treated with shampoo compositions as set forth below:

| Ingredient | Natural ash blonde | Warm golden brown | Light Golden brown | Medium Golden brown | Reddish blonde | Reddish golden blonde |
|---|---|---|---|---|---|---|
| | | | w/w % | | | |
| Water | QS | QS | QS | QS | QS | QS |
| Erythorbic acid | 0.50 | 0.50 | 0.50 | 0.50 | 0.50 | 0.50 |

-continued

| Ingredient | Natural ash blonde | Warm golden brown | Light Golden brown | Medium Golden brown | Reddish blonde | Reddish golden blonde |
|---|---|---|---|---|---|---|
| | | | w/w % | | | |
| Sodium sulfite | 0.50 | 0.50 | 0.50 | 0.50 | 0.50 | 0.50 |
| Ethoxydiglycol | 2.00 | 2.00 | 2.00 | 2.00 | 2.00 | 2.00 |
| P-phenylenediamine | 0.38 | 2.00 | 2.00 | 2.00 | 0.49 | — |
| N,N Bis(2hydroxyethyl)-P-(Paraphenylenediamine) sulfate | 0.12 | — | — | — | — | — |
| P-aminophenol | — | | | | 0.76 | 0.9 |
| Resorcinol | 0.31 | 1.1 | 1.00 | 1.20 | | |
| 4-amino-2-hydroxytoluene | — | 0.1 | — | 0.05 | 0.42 | 0.85 |
| M-aminophenol | 0.04 | 0.8 | — | 0.60 | 0.42 | — |
| 1-Naphthol | 0.09 | — | — | — | — | — |
| 2-methyl resorcinol | — | — | — | — | — | 0.2 |
| Hydroxypropylmethylcellulose | 0.30 | 0.30 | 0.30 | 0.30 | 0.30 | 0.30 |
| Tetrasodium EDTA | 0.30 | 0.30 | 0.30 | 0.30 | 0.30 | 0.30 |
| Sodium lauryl sulfate (30% in water) | 10.00 | 10.00 | 10.00 | 10.00 | 10.00 | 10.00 |
| Sodium laureth sulfate (28% in water) | 20.00 | 20.00 | 20.00 | 20.00 | 20.00 | 20.00 |
| Cocamidopropyl betaine (35%) | 4.00 | 4.00 | 4.00 | 4.00 | 4.00 | 4.00 |
| Ethanolamine | 2.50 | 2.50 | 2.50 | 2.50 | 2.50 | 2.50 |
| Isostearic acid | 6.00 | 6.00 | 6.00 | 6.00 | 2.50 | 2.50 |
| Lauramide DEA (82–86%) | 2.00 | 2.00 | 2.00 | 2.00 | 2.00 | 2.00 |
| Fragrance oil | 0.75 | 0.75 | 0.75 | 0.75 | 0.75 | 0.75 |

The swatches were wet with water and shampooed with the above compositions for 2 minutes, then rinsed well with water. The conditioner composition containing five volume hydrogen peroxide was applied to the hair for 2 minutes then rinsed with water. The resulting hair swatches had vibrant tones and colors. The differences in color and tonality of the treated and control swatches were measured on the color computer, noting the L, a, and b values were measured on all the hair swatches using the DataColor spectrocolorimeter.

| Type | L | a | b |
|---|---|---|---|
| I. Light brown virgin hair treated with Frost & Glow bleach treatment (from above) | 63.53 | 8.01 | 30.68 |
| I. above + Natural Ash Blonde | 55.44 | 7.04 | 23.2 |
| I. above + Warm Golden Brown | 31.23 | 7.04 | 11.06 |
| I. above + Light Golden Brown | 38.38 | 6.08 | 18.21 |
| I. above + Medium Golden Brown | 29.08 | 6.68 | 11.72 |
| I. above + Reddish Blonde | 47.71 | 12.58 | 22.59 |
| I above + Reddish Golden Blonde | 58.71 | 12.97 | 31.25 |

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A method for oxidatively coloring hair comprising:
   (a) applying to the hair fibers a first composition comprising at least one oxidative dye operable to color hair when reacted with an oxidizing agent, said first composition being free of such oxidizing agent and thereby inoperative, by itself, to color hair;
   (b) removing said first composition from the hair but leaving residual oxidative dye in contact with the hair fibers;
   (c) applying, for a time, and in an amount sufficient to color the hair, a second composition to the hair fibers comprising at least one oxidizing agent reactive with the at least one oxidative dye in contact with the hair fibers after removal of the first composition.

2. The method of claim 1 wherein the first composition has a pH ranging from about 7.0 to about 12.0.

3. The method of claim 1 wherein the first composition is a shampoo.

4. The method of claim 1 wherein the first composition is a shampoo comprising water, at least one cleansing surfactant, at least one primary intermediate, and, optionally, at least one coupler.

5. The method of claim 1 wherein the first composition is a shampoo composition comprising, by weight of the total composition:
   about 0.1–55% cleansing surfactant,
   about 0.001–40% of at least one primary intermediate,
   about 0.0001–40% of at least one coupler; and
   about 1–99% water.

6. The method of claim 1 wherein the shampoo composition comprises, by weight of the total composition,
   about 0.1–55% of a cleansing surfactant selected from the group consisting of anionic, amphoteric, zwitterionic, and mixtures thereof,
   about 0.001–40% of at least one primary intermediate,
   about 0.0001–40% of at least one coupler; and
   about 1–99% water.

7. The method of claim 6 wherein the cleansing surfactant comprises an anionic surfactant.

8. The method of claim 7 wherein the anionic surfactant is an alkyl sulfate, alkyl ether sulfate, or mixtures thereof.

9. The method of claim 1 wherein the second composition comprises a hair conditioner.

10. The method of claim 1 wherein the second composition comprises a shampoo or hair conditioner having a pH ranging from about 3.0 to 6.0.

11. The method of claim 1 wherein the second composition is a hair conditioner comprising water, at least one oxidizing agent, and at least one conditioning agent.

12. The method of claim 1 wherein the second composition is a hair conditioner comprising, by weight of the total composition:
about 1–95% water,
about 0.1–55% oxidizing agent, and
about 0.01–45% conditioning agent.

13. The method of claim 1 wherein the first composition is removed from the hair by rinsing with water.

14. The method of claim 1 wherein the first composition is a hair conditioner and the second composition is a shampoo.

15. A kit containing a shampoo and conditioner composition for restoring and rejuvenating the color of the hair, said kit comprised of:
(a) a first container containing a shampoo composition comprising at least one oxidative dye operable to color hair when reacted with an oxidizing agent, said shampoo composition being free of such oxidizing agent and thereby inoperative, by itself, to color hair;
(b) a second container containing a conditioner composition comprising at least one oxidizing agent reactive with the at least one oxidative dye present in the shampoo composition.

16. The kit of claim 15 wherein the shampoo composition contains dyes that provide Level 1 through Level 10 hair color.

17. The kit of claim 15 wherein the conditioner composition has a hydrogen peroxide concentration of about 1 to 30 volume.

18. The kit of claim 15 wherein the conditioner composition has a hydrogen peroxide concentration ranging from about 1 to 10 volume.

19. The kit of claim 15 wherein the conditioner composition has a hydrogen peroxide concentration of about 5 volume.

* * * * *